United States Patent [19]

Cho et al.

[11] Patent Number: 5,530,009
[45] Date of Patent: Jun. 25, 1996

[54] BIS-PIPERIDINYL NON-PEPTIDYL NEUROKININ RECEPTOR ANTAGONISTS

[75] Inventors: Sung Yong S. Cho, Indianapolis; James D. Copp, Greenwood; Francis O. Ginah; Guy J. Hansen, both of Indianapolis; Philip A. Hipskind, New Palestine; Bret E. Huff, Mooresville; Michael J. Martinelli; Michael A. Staszak, both of Indianapolis; Roger W. Tharp-Taylor, Noblesville, all of Ind.

[73] Assignee: Eli Lilly and Company, Indianapolis, Ind.

[21] Appl. No.: 462,413

[22] Filed: Jun. 5, 1996

Related U.S. Application Data

[62] Division of Ser. No. 271,708, Jul. 12, 1994.

[51] Int. Cl.[6] .................. A61K 31/445; C07D 401/14
[52] U.S. Cl. ............................ 514/316; 546/187
[58] Field of Search ........................ 514/316; 546/187

[56] References Cited

U.S. PATENT DOCUMENTS

| 4,751,506 | 6/1988 | Ciganek et al. | 546/44 |
| 5,182,282 | 1/1993 | Clemence | 514/253 |
| 5,300,648 | 4/1994 | Emonds-Alt | 546/193 |
| 5,350,852 | 9/1994 | Emonds-Alt | 544/336 |
| 5,446,052 | 8/1995 | Emonds-Alt | 514/318 |

OTHER PUBLICATIONS

Budurow et al. *Tetrahedron Letters*, vol. 30, pp.2321–2324 (1989).
Chen et al, *Can. J. Chem.* 65 pp. 611–625 (1987).
Nagasaka et al, *Heterocycles* 27, pp. 2219–2224 (1988).
Strazewski et al, *Synthesis*, pp. 218–249 (1987).
Hispskind et al. "Pharmacological characterization of LY 303870: a novel potent and selective nonpeptide substance P receptor antagonist" Pharmcol. Exp. Ther. v. 275, pp. 737–744 (1995).

*Primary Examiner*—Ceila Chang
*Attorney, Agent, or Firm*—Paul J. Gaylo; David E. Boone

[57] ABSTRACT

This invention provides novel compound of the formula

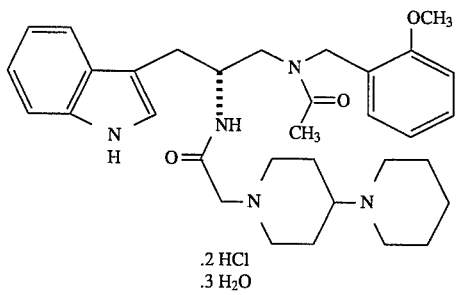

.2 HCl
.3 H₂O which is neurokinin receptor antagonist.

3 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Phe  Xaa  Phe  Leu  Met
1                    5

( 2 ) INFORMATION FOR SEQ ID NO:2:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Arg  Pro  Lys  Arg  Gln  Gln  Phe  Phe  Gly  Leu  Met
1                    5                              10

( 2 ) INFORMATION FOR SEQ ID NO:3:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

His  Lys  Thr  Asp  Ser  Phe  Val  Gly  Leu  Met
1                    5                         10

( 2 ) INFORMATION FOR SEQ ID NO:4:

( i ) SEQUENCE CHARACTERISTICS:
( A ) LENGTH: 10 amino acids
( B ) TYPE: amino acid
( C ) STRANDEDNESS: single
( D ) TOPOLOGY: linear -continued ( i i ) MOLECULE TYPE: peptide ( x i ) SEQUENCE DESCRIPTION: SEQ ID NO:4:

```
Asp Met His Asp Phe Phe Val Gly Leu Met
 1               5                       10
```

BIS-PIPERIDINYL NON-PEPTIDYL NEUROKININ RECEPTOR ANTAGONISTS

This application is a division, of application Ser. No. 08/271,708 filed Jul. 12, 1994.

BACKGROUND OF THE INVENTION

Tachykinins are a family of peptides which share the common amidated carboxy terminal sequence,

hereinafter referred to as SEQ ID NO:1. Substance P was the first peptide of this family to be isolated, although its purification and the determination of its primary sequence did not occur until the early 1970's. Substance P has the following amino acid sequence,

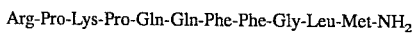

hereinafter referred to as SEQ ID NO:2.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, peptides, 6 (Supplement 3):237–243 (1985) for a review of these discoveries. Neurokinin A has the following amino acid sequence,

hereinafter referred to as SEQ ID NO:3. The structure of neurokinin B is the amino acid sequence,

hereinafter referred to as SEQ ID NO:4.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

In essence, this invention provides processes for preparing a class of potent non-peptidyl tachykinin receptor antagonists. By virtue of their non-peptidyl nature, the compounds of the present invention do not suffer from the shortcomings, in terms of metabolic instability, of known peptide-based tachykinin receptor antagonists.

SUMMARY OF THE INVENTION

This invention provides novel processes for preparing compounds of Formula I

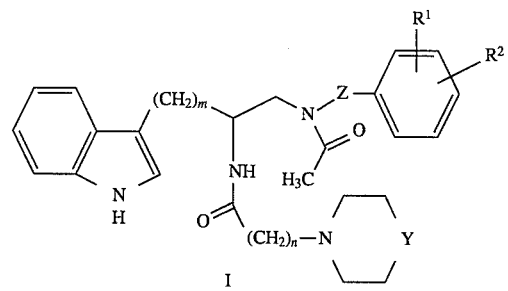

wherein:

m and n are independently 0–6;

Z is $-(CHR^4)_p-(CHR^6)_q-$, where, p is 0 or 1;

q is 0 or 1; and $R^4$ and $R^6$ are independently selected from the group consisting of hydrogen and $C_1-C_3$ alkyl;

Y is

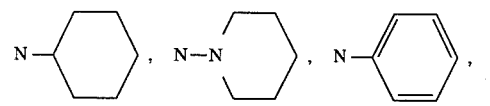

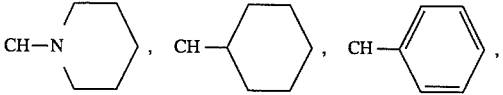

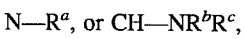

where $R^a$, $R^b$, and $R^c$ are independently selected from the group consisting of hydrogen and $C_1-C_6$ alkyl; and $R^1$ and $R^2$ are independently hydrogen, halo, $C_1-C_6$ alkoxy, $C_1-C_6$ alkylthio, nitro, trifluoromethyl, or $C_1-C_6$ alkyl;

or a pharmaceutically acceptable salt or solvate thereof, which comprises reacting a compound of Formula IIa

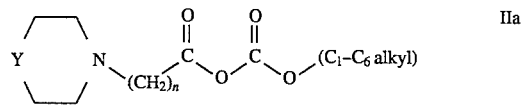

with a compound of Formula III

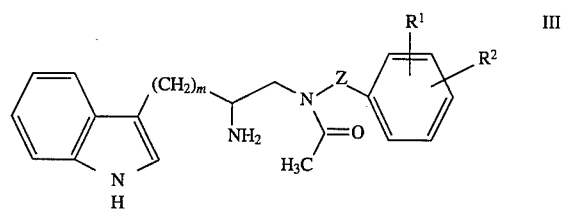

or a salt thereof, optionally in the presence of a base.

In a preferred embodiment this invention provides novel processes for preparing compounds of Formula I

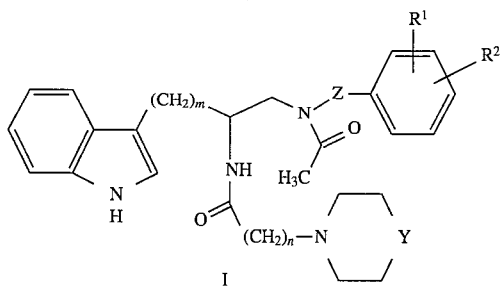

I wherein:

m and n are independently 0–6;

Z is —(CHR$^4$)$_p$—(CHR$^6$)$_q$—, where, p is 0 or 1;

q is 0 or 1; and

R$^4$ and R$^6$ are independently selected from the group consisting of hydrogen and C$_1$–C$_3$ alkyl;

Y is

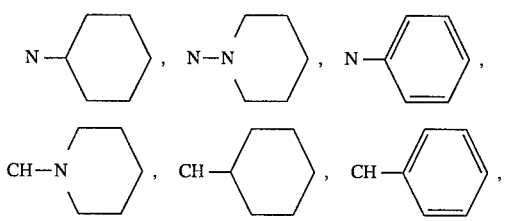

N—R$^a$, or CH—NR$^b$R$^c$, where R$^a$, R$^b$, and R$^c$ are independently selected from the group consisting of hydrogen and C$_1$–C$_6$ alkyl; and R$^1$ and R$^2$ are independently hydrogen, halo, C$_1$–C$_6$ alkoxy, C$_1$–C$_6$ alkylthio, nitro, trifluoromethyl, or C$_1$–C$_6$ alkyl;

or a pharmaceutically acceptable salt or solvate thereof, which comprises reacting a compound of Formula II

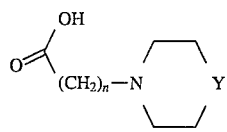

II or a salt thereof, with a suitable haloformate and then reacting the resulting intermediate with a compound of Formula III

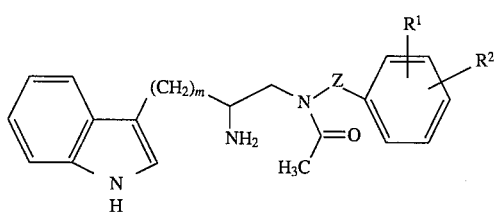

III or a salt thereof, optionally in the presence of a base.

This invention also provides the novel intermediates of the formula

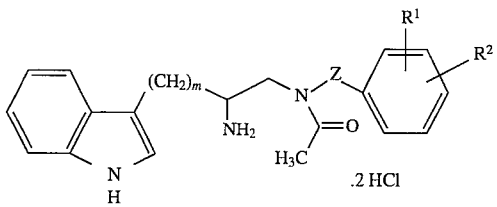

wherein:

m is 0–6;

Z is —(CHR$^4$)$_p$—(CHR$^6$)$_q$—, where, p is 0 or 1;

q is 0 or 1; and

R$^4$ and R$^6$ are independently selected from the group consisting of hydrogen and C$_1$–C$_3$ alkyl; and R$^1$ and R$^2$ are independently hydrogen, halo, C$_1$–C$_6$ alkoxy, C$_1$–C$_6$ alkylthio, nitro, trifluoromethyl, or C$_1$–C$_6$ alkyl.

In another embodiment this invention also provides the novel intermediates of Formula II, or a salt thereof.

DETAILED DESCRIPTION AND PREFERRED EMBODIMENTS

The terms and abbreviations used in the instant examples have their normal meanings unless otherwise designated. For example "°C." refers to degrees Celsius; "N" refers to normal or normality; "mol" refers to mole or moles; "mmol" refers to millimole or millimoles; "g" refers to gram or grams; "kg" refers to kilogram or kilograms; "L" refers to liter or liters; "ml" means milliliter or milliliters; "M" refers to molar or molarity; "MS" refers to mass spectrometry; and "NMR" refers to nuclear magnetic resonance spectroscopy.

As used herein, the term "C$_1$–C$_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "C$_1$–C$_6$ alkyl" includes within its definition the term "C$_1$–C$_3$ alkyl".

"Halo" represents chloro, fluoro, bromo or iodo.

The term "haloformate" as used herein refers to an ester of a haloformic acid, this compound having the formula

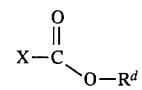

wherein X is halo, and R$^d$ is C$_1$–C$_6$ alkyl. Preferred haloformates are bromoformates and chloroformates. Especially preferred are chloroformates. Those haloformates wherein R$^d$ is C$_3$–C$_6$ are especially preferred. Most preferred is isobutylchloroformate.

"C$_1$–C$_6$ alkylthio" represents a straight or branched alkyl chain having from one to six carbon atoms attached to a sulfur atom. Typical C$_1$–C$_6$ alkylthio groups include methylthio, ethylthio, propylthio, isopropylthio, butylthio and the like.

"C$_1$–C$_6$ alkoxy" represents a straight or branched alkyl chain having from one to six carbon atoms attached to an oxygen atom. Typical C$_1$–C$_6$ alkoxy groups include methoxy, ethoxy, propoxy, isopropoxy, butoxy, t-butoxy, pentoxy and the like.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbony 4-chlorbenzyloxycarbonyl 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl 2-methylcyclohexanyloxycarbonyl, 2-(4-toluylsulfonyl)ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (t-BOC), allyloxycarbonyl and benzyloxycarbonyl. Further examples of groups referred to by the above terms are described by E. Haslam, "Protective Groups in Organic Chemistry", (J. G. W. McOmie, ed., 1973), at Chapter 2; and T. W. Greene and P. G. M. Wuts, "Protective Groups in Organic Synthesis" (1991), at Chapter 7. Throughout the preparations and discussed infra, tritylation, or the addition of a trityl(triphenylmethyl) group is frequently described. This depiction is merely illustrative, the skilled practitioner understanding that other amino-protecting groups described supra may be employed instead.

The compounds employed and prepared in the processes of the present invention may have multiple asymmetric centers. As a consequence of these chiral centers, the compounds produced in the present invention occur as racemates, mixtures of enantiomers and as individual enantiomers, as well as diastereomers and mixtures of diastereomers. Processes for preparing such asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles Practice", (J. H. Fletcher, et al., eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

As noted supra, this invention includes processes for preparing the salts of the compounds defined by Formula I as well as the salts of the compounds of Formulas II and III. A compound employed or prepared in this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

It should be recognized that the particular counterion forming a part of any salt of this invention is usually not of a critical nature, so long as the counterion does not contribute undesired qualities to the salt as a whole.

This invention further encompasses the processes for preparing the pharmaceutically acceptable solvates of the compounds of Formulas I. Many of the Formula I compounds can combine with solvents such as water, methanol, ethanol and acetonitrile to form pharmaceutically acceptable solvates such as the corresponding hydrate, methanolate, ethanolate and acetonitrilate.

The term "optionally in the presence of a base" indicates that the reaction may be performed with a base present, but such a base is not required for the reaction to proceed. Preferred bases include organic bases containing one or more nitrogen groups, such as N-methylmorpholine, ethylamine, diethylamine, triethylamine, ethyldiisopropylamine, polyvinyl pyridine, pyridine, and the like. Especially preferred are N-methylmorpholine and pyridine. The absence of a base is usually most preferred.

In preferred embodiments the preferred processes of the present invention are those processes which result in the synthesis of those compounds of Formula I in which at least one of $R^1$ and $R^2$ is halo, methyl, ethyl, trifluoromethyl, methoxy, or ethoxy. In an especially preferred embodiment the processes of the present invention are those processes which result in the synthesis of those compounds in which one of $R^1$ and $R^2$ is hydrogen and the other is methoxy, chloro, trifluoromethyl, or methyl. In another preferred embodiment the processes of the present invention are those processes which result in the synthesis of those compounds in which both $R^1$ and $R^2$ are independently selected from the group consisting of chloro, methyl, methoxy, and trifluoromethyl.

Especially preferred embodiments of the present invention are those processes which result in the synthesis of those compounds in which one of $R^1$ and $R^2$ is hydrogen and the other is chloro, methyl, methoxy, or trifluoromethyl, substituted at the 2-position of the phenyl group. Another group of especially preferred embodiments of the present invention are those processes of the present invention are those processes which result in the synthesis of those compounds of Formula I in which both $R^1$ and $R^2$ are independently selected from the group consisting of chloro, methyl, methoxy, and trifluoromethyl and they are substituted at the 3 and 5 positions of the phenyl group.

Preferred embodiments of the present invention are those processes which result in the synthesis of those compounds of Formula I in which Y, when combined with the nitrogen-containing heterocycle to which it is attached results in the formation of a sidechain selected from the group consisting of 4-(piperidin-1-yl)piperidine, 4-phenylpiperidine, 4-phenylpiperazine, 4cyclohexylpiperazine, 4-cyclohexylpiperidine, 4-(N,N-dimethylamino)piperidine, and 4-(N,N-diethylamino)piperidine.

The processes of the present invention are usually performed in a non-reactive solvent suitable for the temperatures employed in the reactions. Generally preferred are non-polar solvents with methylene chloride being especially preferred.

The compounds of Formula III can be prepared by a variety of means which are known in the art. Two such synthesis protocols are described in Schemes I and II, infra.

Scheme I

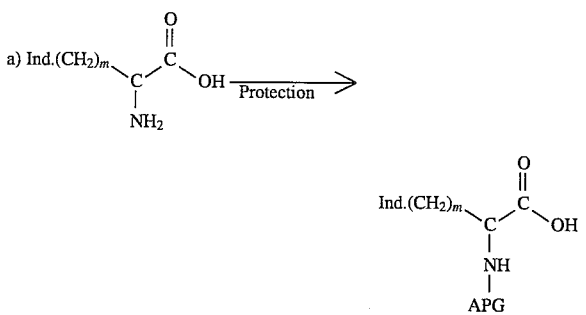

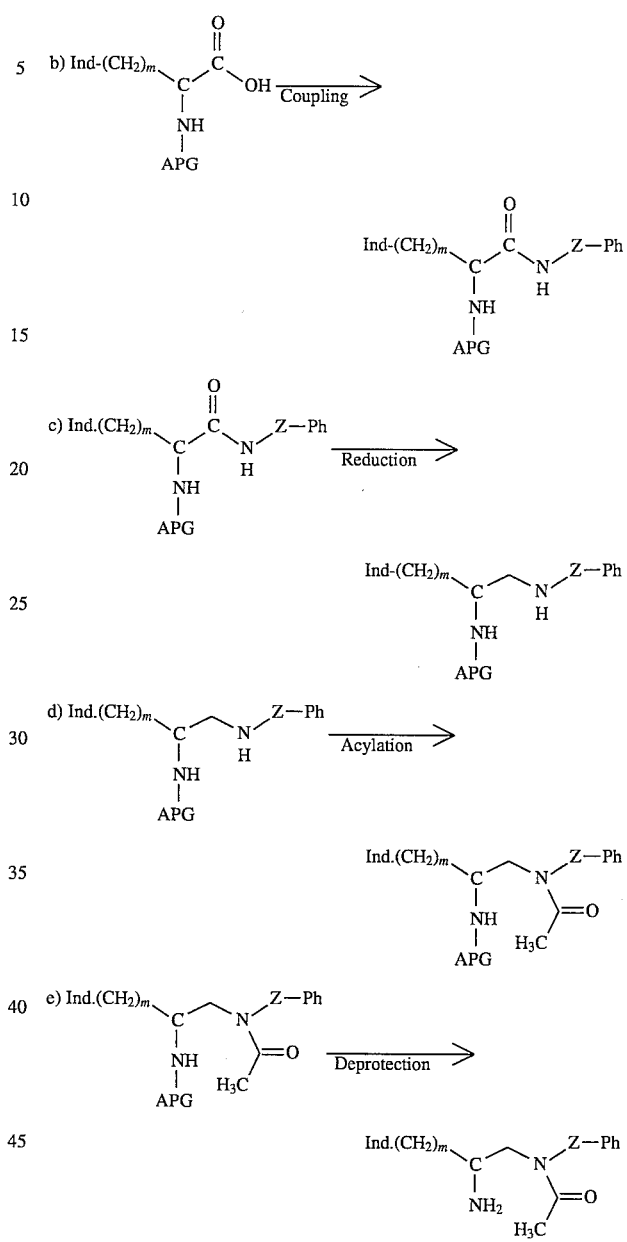

wherein "APG" and is an amino-protecting group, represents $R^1,R^2$-substituted phenyl, and "Ind" represents and indole group.

Scheme II

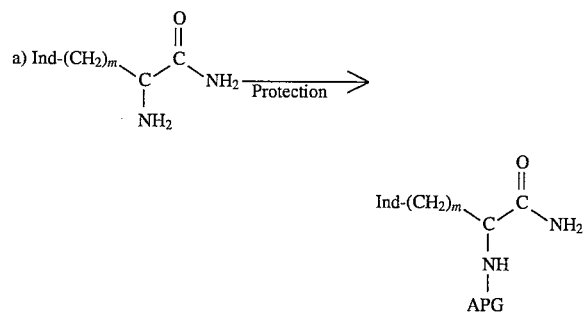

-continued
Scheme II

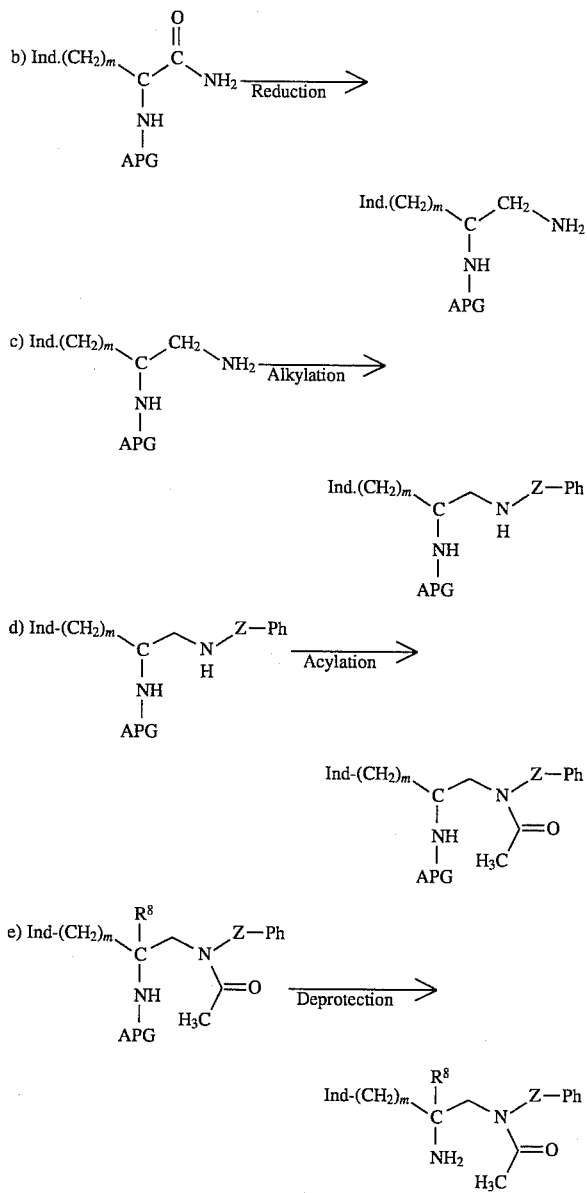

The coupling of the substituted amine can be performed by many means known in the art, the particular methods employed being dependent upon the particular compound used as the starting material and the type of substituted amine used in the coupling reaction. These coupling reactions frequently employ commonly used coupling reagents such as 1,1-carbonyl diimidazole, 1-ethyl-3-(3-dimethylaminopropyl)carbodiimide monohydrate, dicyclohexylcarbodiimide, diethyl azodicarboxylate, 1-hydroxybenzotriazole, alkyl chloroformate and an amine base, phenyldichlorophosphate, and chlorosulfonyl isocyanate. Examples of these methods are described infra.

The intermediate amides are reduced to amines using procedures well known in the art. These reductions can be performed using lithium aluminum hydride as well as by use of many other different aluminum-based hydrides. An especially preferred reagent employed in this reduction is RED-AL®, which is the tradename of a 3.4M solution of sodium bis(2-methoxyethoxy)aluminum hydride in toluene. Alternatively, the amides can be reduced by catalytic hydrogenation, though high temperatures and pressures are usually required for this. Sodium borohydride in combination with other reagents may be used to reduce the amide. Borane complexes, such as a borane dimethylsulfide complex, are especially useful in this reduction reaction.

The acylation of the secondary amine can be done using any of a large number of techniques regularly employed by those skilled in organic chemistry. One such reaction scheme is a substitution using an anhydride such as acetic anhydride. Another reaction scheme often employed to acylate a secondary amine employs a carboxylic acid preferably with an activating agent. An amino-dealkoxylation type of reaction uses esters as a means of acylating the amine. Activated esters which are attenuated to provide enhanced selectivity are very efficient acylating agents. One preferred such activated ester is p-nitrophenyl ester, such as p-nitrophenyl acetate.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active acid or base. These diastereomers can then be separated using differential solubility, fractional crystallization, chromatography, or like methods. Further details regarding resolution of enantiomeric mixtures can be found in J. Jacques, et al., "Enantiomers, Racemates, and Resolutions", (1991).

In addition to the schemes described above, the practitioner of this invention may also choose an enantiospecific protocol for the preparation of the compounds of Formula III. Such a protocol employs a synthetic reaction design which maintains the chiral center present in the starting material in a desired orientation. These reaction schemes usually produce compounds in which greater than 95 percent of the title product is the desired enantiomer. Such a protocol begins with a specific enantiomer, such as (R)-(+)-tryptophan (also known as D-tryptophan). Subsequent reaction steps are performed so as not to destroy the chiralty. Such enantiospecific syntheses are the preferred embodiment of this invention. One example of such a protocol is depicted in Scheme III, infra.

Scheme III

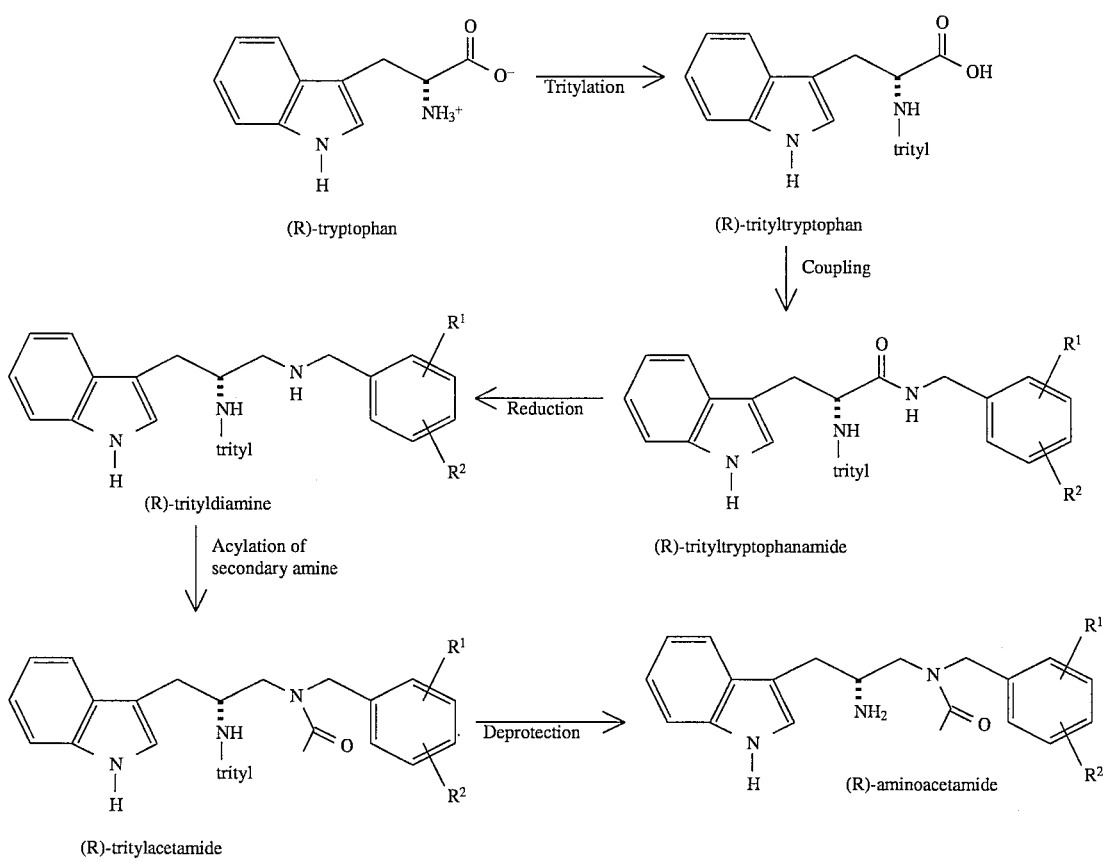

The following preparations and examples are illustrative of the processes and intermediates of the present invention. The preparations and examples do not limit the scope of this invention in any way.

Preparation 1

Tritylation

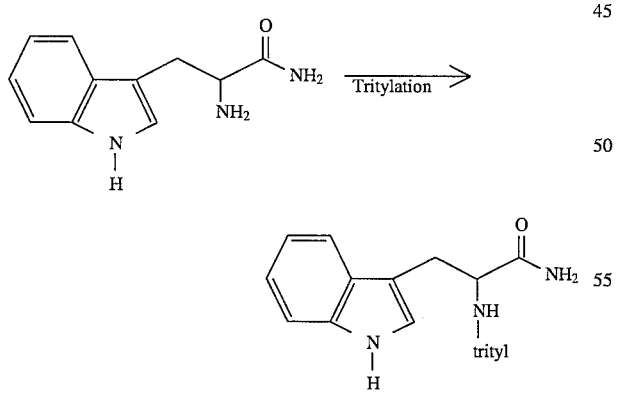

Preparation of 3-(1H-indol-3-yl)-2-(N-triphenylmethylamino)propanamide.

Tryptophan amide (26.43 g, 0.130 mol) was suspended in 260 ml of methylene chloride and this mixture was flushed with nitrogen and then put under argon. Trityl chloride (38.06 g, 0.136 mol) was dissolved in 75 ml of methylene chloride. The trityl chloride solution was slowly added over 25 minutes to the stirred tryptophan amide solution immersed in an ice bath. The reaction mixture was then allowed to stir overnight at room temperature.

The reaction mixture was poured into a separation funnel and was washed with 250 ml of water, followed by 250 ml of brine. As the organic layer was filtering through sodium sulfate to dry, a solid precipitated. The filtrate was collected and the solvent was evaporated.

Ethyl acetate was then added to the combined solid and this mixture was stirred and then refrigerated overnight. The next day the resulting solid was filtered, washed several times with cold ethyl acetate, and then dried in vacuo. Yield 49.76 g (85.9%).

Preparation 2

Reduction of Carbonyl

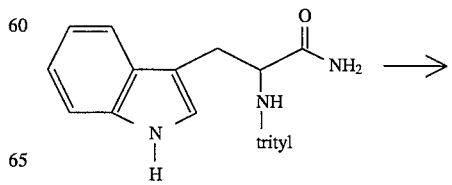

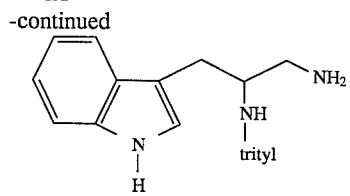

Preparation of 1-amino-3-(1H-indol-3-yl)-2-(N-triphenylmethylamino)propane

Under argon the 3-(1H-indol-3-yl)-2-(N-triphenylmethylamino)propanamide (48.46 g, 0.108 mol) was suspended in 270 ml of tetrahydrofuran. This mixture was heated to reflux. Borane-methyl sulfide complex (41.3 g, 0.543 mol) was then slowly added to the reaction mixture. All of the starting amide dissolved during the addition of the borane-methyl sulfide complex. This solution was then stirred overnight in an 83° C. oil bath.

After cooling to room temperature a 1:1 mixture of tetrahydrofuran:water (75 ml total) was added to the solution. Sodium hydroxide (5N, 230 ml) was then added to the mixture, which was then heated to reflux for about 30 minutes.

After partitioning the aqueous and organic layers, the organic layer was collected. The aqueous layer was extracted with tetrahydrofuran. The organic layers were combined and the solvents were then removed by evaporation. The resulting liquid was then partitioned between ethyl acetate and brine and was washed a second time with brine. The solution was then dried over sodium sulfate and the solvents were removed in vacuo to yield 48.68 grams of the desired intermediate.

Preparation 3

Alkylation of primary amine

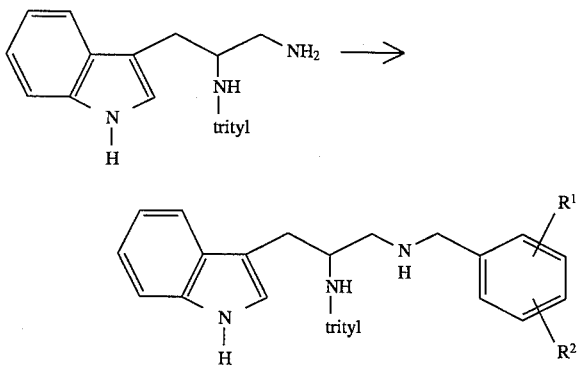

Preparation of 1-[N-(2-methoxybenzyl)amino]-3-(1H-indol-3 yl)- 2-(N-triphenylmethylamino)propane To a mixture of 1-amino-3-(1H-indol-3-yl)-2-(N-triphenylmethylamino)propane (48.68 g, 0.109 mol) dissolved in toluene (1.13 l) was added 2-methoxybenzaldehyde (23.12 g, 0.169 mol), the 2-methoxybenzaldehyde having been previously purified by base wash. The reaction mixture was stirred overnight. The solvents were then removed in vacuo.

The recovered solid was dissolved in 376 ml of a 1:1 tetrahydrofuran:methanol mixture. To this solution was added sodium borohydride (6.83 g, 0.180 mol). This mixture was stirred on ice for about 4 hours. The solvents were removed by evaporation. The remaining liquid was partitioned between 1200 ml of ethyl acetate and 1000 ml of a 1:1 brine:2N sodium hydroxide solution. This was extracted with ethyl acetate (2×500 ml) and then dried over sodium sulfate. The solvents were then removed by evaporation overnight, yielding 67.60 grams (>98% yield) of the desired product. FDMS 552 ($M^{+1}$).

Preparation 4

Tritylation

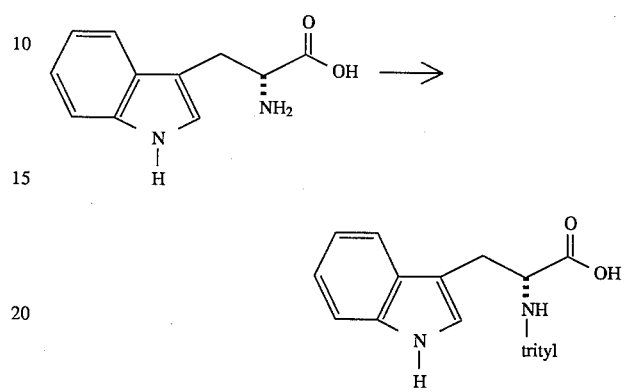

Preparation of (R)-3-(1H-indol-3-yl)-2-(N-triphenylmethylamino)propanoic acid [N-trityltryptophan]

Chlorotrimethylsilane (70.0 ml, 0.527 mol) was added at a moderate rate to a stirred slurry of D-tryptophan (100.0 g, 0.490 mol) in anhydrous methylene chloride (800 ml) under a nitrogen atmosphere. This mixture was continuously stirred for 4.25 hours. Triethylamine (147.0 ml, 1.055 mol) was added, followed by the addition of a solution of triphenylmethyl chloride (147.0 g, 0.552 mol) in methylene chloride (400 ml) using an addition funnel. The mixture was stirred at room temperature, under a nitrogen atmosphere for at least 20 hours. The reaction was quenched by the addition of methanol (500 ml).

The solution was concentrated on a rotary evaporator to near dryness and the mixture was redissolved in methylene chloride and ethyl acetate. An aqueous work-up involving a 5% citric acid solution (2×) and brine (2×) was then performed. The organic layer was dried over anhydrous sodium sulfate, filtered, and concentrated to dryness on a rotary evaporator. The solid was dissolved in hot diethyl ether followed by the addition of hexanes to promote crystallization. By this process 173.6 g (0.389 mol) of analytically pure (R)-3-(1H-indol-3-yl)-2-(N-triphenylmethylamino)propanoic acid was isolated as a white solid in two crops giving a total of 79% yield.

FDMS 446 ($M^+$). $^1H$ NMR (DMSO-$d_6$) δ2.70 (m, 1H), 2.83 (m, 2H), 3.35 (m, 1H), 6.92–7.20 (m, 12H), 7.30–7.41 (m, 8H), 10.83 (s, 1H), 11.73 (br s, 1H).

Analysis for $C_{30}H_{26}N_2O_2$: Theory: C, 80.69; H, 5.87; N, 6.27. Found: C, 80.47; H, 5.92; N, 6.10.

Preparation 5

Coupling

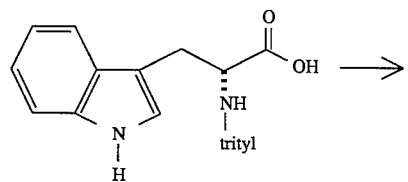

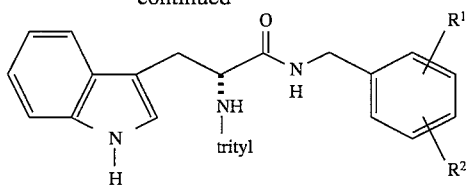

Preparation of (R)-3-(1H-indol-3-yl)-N-(2-methoxybenzyl)-2 -(N-triphenylmethylamino)propanamide To a stirred solution of (R)-3-(1H-indol-3-yl)-2-(N-triphenylmethylamino)propanoic acid (179.8 g, 0.403 mol), 2-methoxybenzylamine (56.0 ml, 0.429 mol), and hydroxybenzotriazole hydrate (57.97 g, 0.429 mol) in anhydrous tetrahydrofuran (1.7 L) and anhydrous N,N-dimethylformamide (500 ml) under a nitrogen atmosphere at 0° C., were added triethylamine (60.0 ml, 0.430 mol) and 1-(3-dimethylaminopropyl)-3-ethoxycarbodiimide hydrochloride (82.25 g, 0.429 mol). The mixture was allowed to warm to room temperature under a nitrogen atmosphere for at least 20 hours. The mixture was concentrated on a rotary evaporator and then redissolved in methylene chloride and an aqueous work-up of 5% citric acid solution (2×), saturated sodium bicarbonate solution (2×), and brine (2×) was performed. The organic layer-was dried over anhydrous sodium sulfate and concentrated to dryness on a rotary evaporator. The desired product was then recrystallized from hot ethyl acetate to yield 215.8 g (0.381 mol, 95%) of analytically pure material.

FDMS 565 (M$^+$). $^1$H NMR (CDCl$_3$) δ2.19 (dd, J=6.4 Hz, Δv=14.4 Hz, 1H), 2.64 (d, J=6.5 Hz, 1H), 3.19 (dd, J=4.3 Hz, Δv=14.4 Hz, 1H), 3.49 (m, 1H), 3.63 (s, 3H), 3.99 (dd, J=5.4 Hz, Δv=14.2 Hz, 1H), 4.25 (dd, J=7.1 Hz, Δv=14.2 Hz, 1H), 6.64 (d, J=2.1 Hz, 1H), 6.80 (d, J=8.2 Hz, 1H), 6.91 (t, J=7.4 Hz, 1H), 7.06–7.38 (m, 21H), 7.49 (d, J=7.9 Hz, 1H), 7.75 (s, 1H).

Analysis for C$_{38}$H$_{35}$N$_3$O$_2$: Theory: C, 80.68; H, 6.24; N, 7.43. Found: C, 80.65; H, 6.46; N, 7.50.

Preparation 6

Reduction of Carbonyl

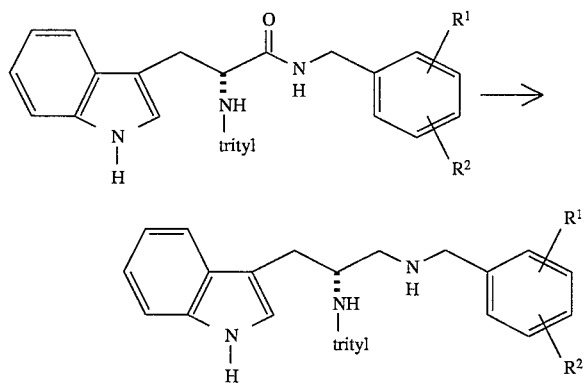

Preparation of (R)-3-(1H-indol-3-yl)-1-[N-(2-methoxybenzyl)amino]- 2-(N-triphenylmethylamino)propane RED-AL®, [a 3.4M, solution of sodium bis(2-methoxyethoxy)aluminum hydride in toluene](535 ml, 1.819 mol), dissolved in anhydrous tetrahydrofuran (400 ml) was slowly added Using an addition funnel to a refluxing solution of the acylation product, (R)-3-(1H-indol-3-yl)-N-(2-methoxybenzyl)- 2-(N-triphenylmethylamino)propanamide (228.6 g, 0.404 mols) produced supra, in anhydrous tetrahydrofuran (1.0 L) under a nitrogen atmosphere. The reaction mixture became a purple solution. The reaction was quenched after at least 20 hours by the slow addition of excess saturated Rochelle's salt solution (potassium sodium tartrate tetrahydrate). The organic layer was isolated, washed with brine (2×), dried over anhydrous sodium sulfate, filtered, and concentrated to an oil on a rotary evaporator. No further purification was done and the product was used directly in the next step.

Preparation 7

Acylation of Secondary Amine

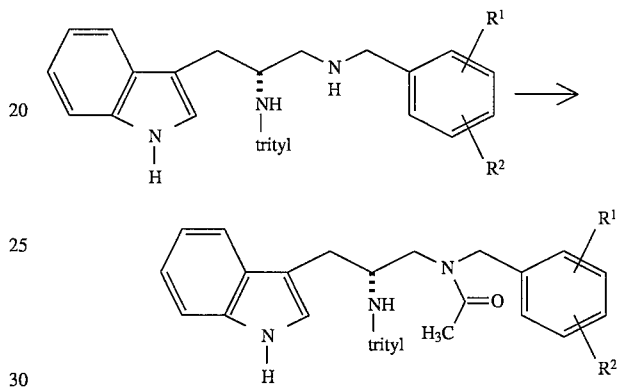

Preparation of (R)-3-(1H-indol-3-yl)-1-[N-(2-methoxybenzyl)-acetylamino]- 2-(N-triphenylmethylamino)propane To a stirring solution of (R)-3-(1H-indol-3-yl)-1-[N-(2-methoxybenzyl)amino]-2-(N-triphenylmethylamino)propane (0.404 mol) in anhydrous tetrahydrofuran (1.2 L) under a nitrogen atmosphere at 0° C. was added triethylamine (66.5 ml, 0.477 mol) and acetic anhydride (45.0 ml, 0.477 mol). After 4 hours, the mixture was concentrated on a rotary evaporator, redissolved in methylene chloride and ethyl acetate, washed with water (2×) and brine (2×), dried over anhydrous sodium sulfate, filtered, and concentrated to a solid on a rotary evaporator. The resulting solid was dissolved in chloroform and loaded onto silica gel 60 (230–400 mesh) and eluted with a 1:1 mixture of ethyl acetate and hexanes. The product was then crystallized from an ethyl acetate/hexanes mixture. The resulting product of (R)-3-(1H-indol-3-yl)-1-[N-(2-methoxybenzyl)acetylamino]-2-(N-triphenylmethylamino)propane was crystallized and isolated over three crops giving 208.97 grams (87% yield) of analytically pure material.

Analysis for C$_{40}$H$_{39}$N$_3$O$_2$: Theory: C, 80.91; H, 6.62; N, 7.08. Found: C, 81.00; H, 6.69; N, 6.94.

Preparation 8

Deprotection

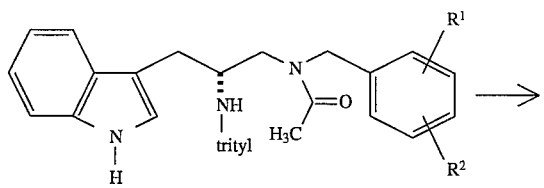

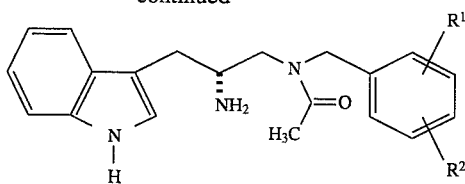

Preparation of (R)-2-amino-3-(1H-indol-3-yl)-1-[N-(2-methoxybenzyl)acetylamino]propane Formic acid (9.0 ml, 238.540 mmol) was added to a stirring solution of (R)-3-(1H-indol-3-yl)-1-[N-(2-methoxybenzyl)methoxybenzyl)acetylamino]- 2-(N-triphenylmethylamino)propane (14.11 g, 23.763 mmol) in anhydrous methylene chloride under a nitrogen atmosphere at 0° C. After 4 hours, the reaction mixture was concentrated to an oil on a rotary evaporator and redissolved in diethyl ether and 1.0N hydrochloric acid. The aqueous layer was washed twice with diethyl ether and basified with sodium hydroxide to a pH greater than 12. The product was extracted out with methylene chloride (4×). The organic extracts were combined, dried over anhydrous sodium sulfate, filtered, and concentrated on a rotary evaporator to a white foam. The compound (R)-2-amino-3-(1H-indol-3-yl)-1-[N-(2-methoxybenzyl)acetylamino]propane (7.52 g, 21.397 mmols) was isolated giving a 90% yield. No further purification was necessary.

EXAMPLE 1

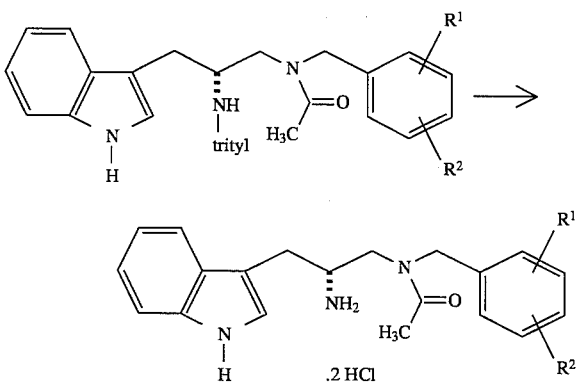

Preparation of (R)-2-amino-3-(1H-indol-3-yl)-1-[N-(2-methoxybenzyl)acetylamino]propane dihydrochloride A stirring solution of (R)-3-(1H-indol-3-yl)-1-[N-(2-methoxybenzyl)acetylamino]-2-(N-triphenylmethylamino)propane in two volumes of methylene chloride was cooled to between −40° C. and −50° C. Anhydrous hydrogen chloride gas was added at such a rate that the temperature of the reaction mixture did not exceed 0° C. The reaction mixture was stirred for 30 minutes to one hour at 0°–10° C.

To this reaction mixture was added two volumes of methyl t-butyl ether and the resulting mixture was allowed to stir for 30 minutes to one hour at 0°–10° C. The resulting crystalline solid was removed by filtration and then washed with methyl t-butyl ether. The reaction product was dried under vacuum at 50° C. (Yield>98%)

Analysis for $C_{21}H_{25}N_3O_2 \cdot 2$ HCl: Theory: C, 59.44; H, 6.41; N, 9.90. Found: C, 60.40; H, 6.60; N, 9.99.

EXAMPLE 2

Preparation of 2-((4-cyclohexyl)piperazin-1-yl)acetic acid potassium salt hydrate Cyclohexylpiperazine (10.0 g, 0.059 mol) was added to ten volumes of methylene chloride at room temperature. To this mixture was added sodium hydroxide (36 ml of a 2N solution, 0.072 mol) and tetrabutylammonium bromide (1.3 g, 0.004 mol). After the addition of the sodium hydroxide and tetrabutylammonium bromide, methyl bromoacetate (7.0 ml, 0.073 mol) was added and the reaction mixture was stirred for four to six hours. The progress of the reaction was monitored by gas chromatography.

The organic fraction was separated and the aqueous phase was back-extracted with methylene chloride. The organic phases were combined and washed twice with deionized water, once with saturated sodium bicarbonate solution, and then with brine. The organic phase was dried over magnesium sulfate and the solvents were removed in vacuo to yield methyl 2-((4-cyclohexyl)piperazin-1-yl)acetate as a yellowish oil.

The title compound was prepared by dissolving the methyl 2-((4-cyclohexyl)piperazin-1-yl)acetate (10.0 g, 0.042 mol) in ten volumes of diethyl ether. This solution was cooled to 15° C. and then potassium trimethylsilanoate (5.9 g, 0.044) was added. This mixture was then stirred for four to six hours. The reaction product was removed by filtration, washed twice with five volumes of diethyl ether, then washed twice with five volumes of hexanes, and then dried in a vacuum oven for 12–24 hours at 50° C.

Analysis for $C_{12}H_{21}KN_2O_2 \cdot 1.5\ H_2O$: Theory: C, 49.63; H, 7.98; N, 9.65. Found: C, 49.54; H, 7.72; N, 9.11.

EXAMPLE 3

Preparation of (R)-2-[N-(2-((4-cyclohexyl)piperazin-1-yl)acetyl)amino]- 3-(1H-indol-3-yl)-1-[N-(2-methoxybenzyl)acetylamino]propane The title compound was prepared by first cooling 2-((4-cyclohexyl)piperazin-1-yl)acetic acid potassium salt to a temperature between −8° C. and −15° C. in 5 volumes of anhydrous methylene chloride. To this mixture was added isobutylchloroformate at a rate such that the temperature did not exceed −8° C. The resulting reaction mixture was stirred for about 1 hour, the temperature being maintained between −8° C. and −15° C.

To this mixture was then added (R)-2-amino-3-(1H-indol-3-yl)-1-[N-(2-methoxybenzyl)acetylamino]propane dihydrochloride at such a rate that the temperature did not exceed 0° C. Next added to this mixture was N-methyl morpholine at a rate such that the temperature did not exceed 0° C. This mixture was then stirred for about 1 hour at a temperature between −15° C. and −8° C.

The reaction was quenched by the addition of 5 volumes of water. The organic layer was washed once with a saturated sodium bicarbonate solution. The organic phase was then dried over anhydrous potassium carbonate and filtered to remove the drying agent. To the filtrate was then added 2 equivalents of concentrated hydrochloric acid, followed by 1 volume of isopropyl alcohol. The methylene chloride was then exchanged with isopropyl alcohol under vacuum by distillation.

The final volume of isopropyl alcohol was then concentrated to three volumes by vacuum. The reaction mixture was cooled to 20° C. to 25° C. and the product was allowed to crystallize for at least one hour. The desired product was then recovered by filtration and washed with sufficient isopropyl alcohol to give a colorless filtrate. The crystal cake was then dried under vacuum at 50° C.

MS 560 (M+1$^+$). $^1$H NMR (CDCl$_3$) δ1.09–1.28 (m, 5H), 1.64 (d, J=10 Hz, 1H), 1.80–1.89 (m, 4H), 2.10 (s, 3H), 2.24–2.52 (m, 9H), 2.90 (s, 2H), 2.95 (d, J=7 Hz, 1H), 3.02 (d, J=7 Hz, 1H), 3.12 (dd, J=5, 14 Hz, 1H), 3.77 (s, 3H), 4.01 (dd, J=10, 14 Hz, 1H), 4.49 (ABq, J=17 Hz, 43 Hz, 2H), 4.56 (m, 1H), 6.79–6.87 (m, 3H), 7.05–7.24 (m, 4H), 7.34–7.41 (m, 2H), 7.67 (d, J=8 Hz, 1H), 8.22 (s, 1H).

Analysis for $C_{33}H_{45}N_5O_3$: Theory: C, 70.81; H, 8.10; N, 12.51. Found: C, 70.71; H, 8.21; N, 12.42.

EXAMPLE 4

Preparation of (R)-3-(1H-indol-3-yl)-1-[N-(2-methoxybenzyl)acetylamino]- 2-[N-(2-(4-(piperidin-1-yl)piperidin-1-yl)acetyl)amino]propane The title compound was prepared by first admixing (R)-2-amino-3-(1H-indol-3-yl)-1-[N-(2-methoxybenzyl)acetylamino]propane dihydrochloride (50.0 g, 0.118 mol) with 100 ml of methylene chloride under a nitrogen atmosphere.

In a second flask, under a nitrogen atmosphere, 2-(4-(piperidin-1-yl)piperidin-1-yl)acetic acid potassium salt (62.3 g, 0.236 mol) was added to 600 ml of methylene chloride. This mixture was cooled to about −10° C. and stirring was continued. To this mixture isobutylchloroformate (23 ml, 0.177 mol) was added dropwise such that the temperature of the 2-(4-(piperidin-1- yl)piperidin-1-yl)acetic acid potassium salt mixture never rose appreciably.

This reaction mixture was stirred at about −10° C. for about 1.5 hours at which time the (R)-2-amino-3-(1H-indol-3-yl)-1-[N-(2-methoxybenzyl)acetylamino]propane dihydrochloride/methylene chloride mixture prepared supra was slowly added to the 2-(4-(piperidin-1-yl)piperidin-1-yl)acetic acid potassium salt/isobutylchloroformate/methylene chloride solution. The resulting mixture was then stirred for about 1 hour at a temperature between −15° C. and −8° C.

The reaction mixture was removed from the ice bath and allowed to warm to 15°–20° C. and the reaction was quenched by the addition of 200 ml of water. The pH of the solution was adjusted to 2.3–2.7 by the addition of 1N sulfuric acid. The layers were separated and the aqueous layer was washed with 100 ml of methylene chloride.

The organic fractions were combined and washed with water (100 ml). The water wash was back extracted with methylene chloride (50 ml) and combined with the aqueous fraction from above. Methylene chloride (500 ml) was added to the combined aqueous layers and the mixture was stirred at room temperature for 15 minutes as basification with 2N sodium hydroxide to a final pH of 9.8 to 10.2 was achieved.

The organic and aqueous fractions were separated. The aqueous fraction was washed with methylene chloride and the methylene chloride was added to the organic fraction. The organic fraction was then washed with a mixture of saturated sodium bicarbonate solution (100 ml) and water (50 ml). The bicarbonate wash was separated from the organic fraction and back extracted with methylene chloride (50 ml). The back extraction was combined with the methylene chloride fraction and the combined fractions were dried over magnesium sulfate. The magnesium sulfate was removed by filtration and the volatiles were removed by vacuum distillation to yield the title product as a foam.

(72.5 g, >98% yield). MS 559 ($M^{+1}$) NMR (DMSO-$d_6$ 3:2 mixture of amide rotamers) δ1.25–1.70 (m, 10H), 1.77–2.00 (m, 2H), 1.95 (s, ⅗•3H), 2.04 (s, ⅖•3H), 2.10–2.97 (m, 9H), 3.10–3.65 (m, 3H), 3.72 (s, ⅖•3H), 3.74 (s, ⅗•3H), 4.26–4.58 (m, 3H), 6.76–7.12 (m, 6H), 7.13–7.35 (m, 2H), 7.42–7.66 (m, 2H), 10.80 (br s, 1H).

Analysis for $C_{33}H_{45}N_5O_3$: Theory: C, 70.81; H, 8.10; N, 12.51. Found: C, 70.57; H, 8.05; N, 12.39.

EXAMPLE 5

Preparation of (R)-3-(1H-indol-3-yl)-1-[N-(2-methoxybenzyl) acetylamino]-2-[N-(2-(4-(piperidin-1-yl) piperidin-1-yl)acetyl)amino]propane dihydrochloride Under a nitrogen atmosphere, 2-(4-(piperidin-1-yl)piperidin-1-yl)acetic acid potassium salt, in ten volumes of anhydrous methylene chloride, was cooled to between −8° C. and −15° C. To this mixture isobutylchloroformate was added at such a rate that the temperature of the reaction mixture never exceeded −8° C. After the addition of the isobutylchloroformate, the reaction mixture was stirred for about ninety minutes while maintaining the temperature between −15° C. and −8° C.

The reaction mixture was then cooled to between −37° C. and −32° C. To this cooled mixture (R)-2-amino-3-(1H-indol-3-yl)-1-[N-(2-methoxybenzyl)acetylamino]propane was added as a solid at a rate such that the temperature of the reaction mixture did not exceed −20° C. After the addition was complete, the reaction mixture was then stirred for about one hour while the temperature was maintained between −30° C. and −20° C.

The reaction was quenched by the addition of five volumes of deionized water. The pH of the reaction mixture was then adjusted to 12.8–13.2 by the addition of 5N sodium hydroxide. The aqueous fraction was removed and extracted with one volume of methylene chloride. The methylene chloride fractions were combined and five volumes of water was added, and the pH was again adjusted to 12.8–13.2 by the addition of 5N sodium hydroxide.

After mixing the methylene chloride and aqueous layers thoroughly, the phases were separated and the aqueous fraction was washed with methylene chloride. The methylene chloride wash was added to the organic fraction from above and the resulting organic fraction was washed four times with deionized water and once with brine. The organic fraction was dried over magnesium sulfate. The magnesium sulfate was removed by filtration. The methylene chloride was replaced with acetone via distillative exchange. Hydrochloric acid (6N) was added and 13 volumes of acetone were slowly added with seeding. The crystal slurry was stirred for about one hour. The resulting crystal slurry was filtered and washed with acetone. The dihydrochloride salt of the product was then dried under vacuum at 50° C. (Yield >98%)

The product of Example 4, the dihydrochloride salt, may be readily converted to the free base using standard techniques. In one preferred such procedure, sodium hydroxide is added to a solution containing the dihydrochloride salt until the pH of the solution is between 11 and 12. The free base is then extracted with organic solvents and purified as previously described.

Preparation 9

Tritylation

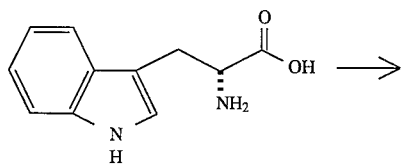

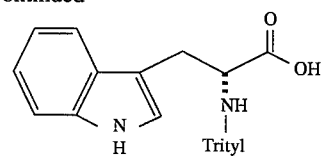

Preparation of (R)-3-(1H-indol-3-yl)-2-(N-triphenylmethylamino) propanoic acid

D-Tryptophan (1.75 kg, 8.57 mol) and chlorotrimethylsilane (1196 ml, 9.43 mol) were added to tetrahydrofuran (8.75 L) under a nitrogen atmosphere. This mixture was heated to reflux and stirred continuously for about four hours. The solution was cooled to 25° C. and triethylamine (2.51 L, 17.9 mol) was added, followed by trityl chloride (2.63 kg, 9.43 mol). This solution was stirred at room temperature for 12–24 hours. The reaction was quenched with the addition of methanol (385 ml) and stirred for fifteen minutes.

To this solution was added methyl t-butyl ether (8.75 L), citric acid (437.5 g, 2.27 mol), and deionized water (8.75 L). This mixture was stirred for fifteen minutes at room temperature, the layers were separated, the organic fraction was washed a second time with citirc acid (437.5 g, 2.27 mol) and deionized water (8.75 L). The aqueous fractions were discarded.

The organic fraction was washed with saturated sodium chloride, dried over anhydrous sodium sulfate, filtered, and concentrated to a foam on a rotary evaporator. To this foam was added refined technical ether (8.75 L) and heptane (8.75 L) at room temperature. The resulting solids were removed by filtration and rinsed with heptane (5.0 L). A second crop was recovered by evaporating the filtrate to dryness on a rotary evaporator, adding refined technical ether (1.0 L) and heptane (1.5 L), and then filtering off the resulting solids. Each crop was then dried, resulting in 3688.6 g (96.6%) of (R)-3-(1H-indol-3-yl)-2-(N-triphenylmethylamino)propanoic acid white solid.

Preparation 10

Coupling

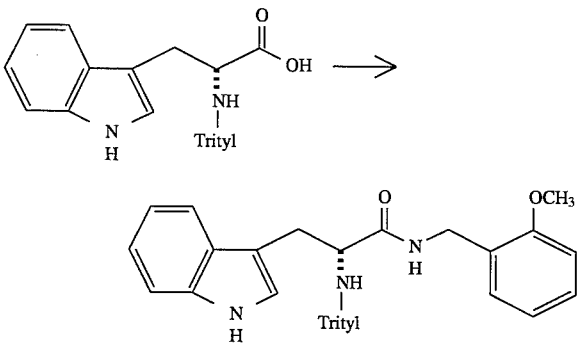

Preparation of (R)-3-(1H-indol-3-yl)-N-(2-methoxybenzyl)-2-(N-triphenylmethylamino)propanamide Under a nitrogen atmosphere (R)-3-(1H-indol-3-yl)-2-(N-triphenylmethylamino)propanoic acid (1.6 kg, 3.58 mol), 1-hydroxybenzotriazole monohydrate (522.45 g, 3.87 mol), 2-methoxybenzylamine (505.14 ml, 3.87 mol), triethylamine (539.35 ml, 3.87 mol), and 1-ethyl-3-(3-dimethylaminopropyl)carbodiimide hydrochloride (741.9 g, 3.87 mol) were added to tetrahydrofuran (12 L). The resulting solution was stirred at room temperature for 20– 28 hours.

The solvents were removed in vacuo, leaving an oily residue.

The residue was redissolved in methylene chloride (10.5 L). This solution was washed with 0.26M citric acid (2×4.0 L), with a saturated sodium bicarbonate solution, and then with brine. The organic fraction was dried over anhydrous magnesium sulfate and the solvents were removed in vacuo. The solid residue was dissolved in ethyl acetate (6.4 L), stirred at room temperature for 15–30 minutes, and then stirred for 1–24 hours at −5° to −10° C. The resulting solids were collected by filtration, washed with cold ethyl acetate (2.0 L) and then dried, yielding 1809.7 g (89.6%) of (R)-3-(1H-indol-3-yl)-N-(2-methoxybenzyl)- 2-(N-triphenylmethylamino)propanamide.

Preparation 11

Reduction of Carbonyl and Acylation of Secondary Amine

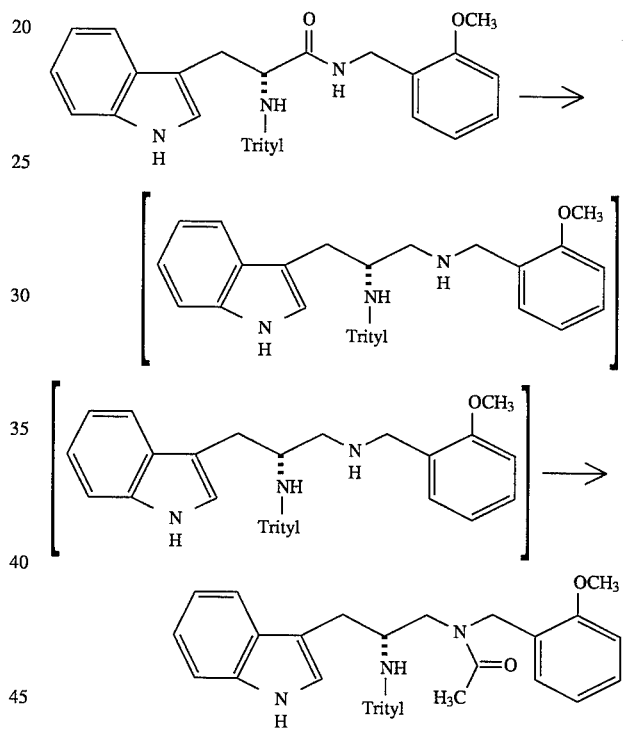

Preparation of 3-(1H-indol-3-yl)-1-[N-(2-methoxybenzyl) acetylamino]-2-(N-triphenylmethylamino)propane Under a nitrogen atmosphere (R)-3-(1H-indol-3-yl)-N-(2-methoxybenzyl)-2-(N-triphenylmethylamino)propanamide (1166 g, 2.06 mol) was added to toluene (8.25 L). RED-AL®[a 3.4M solution of sodium bis(2-methoxyethoxy)aluminum hydride in toluene](2728 ml, 9.27 mol) was slowly added to this solution and the solution was heated to reflux and stirred for 1–8 hours. The reaction mixture was cooled to 0°–10° C. and the reaction was quenched by adding deionized water (1.4 L). The resulting mixture was stirred for 15–30 minutes between 0° C. and room temperature. The resulting solids were removed by filtration, rinsed with toluene (1.0 L) and discarded.

The filtrate and rinse were combined and dried over anhydrous magnesium sulfate. The resulting solution was cooled to 0°–5° C. and triethylamine (311.7 ml, 2.25 mol) and acetic anhydride (211.1 ml, 2.25 mol) were slowly added between 0° C. and room temperature. After this addition, the solution was allowed to warm to room temperature and stirred at room temperature for 1–24 hours. The reaction was quenched by the addition of deionized water (2.0 L). The layers were separated and the aqueous fraction was discarded.

The organic fraction was washed with a saturated sodium bicarbonate solution (2×2.0 L) and then with a saturated sodium chloride solution (2.0 L). The organic fraction was dried over anhydrous magnesium sulfate, and the solvents were removed in vacuo, yielding an oil. The residue was dissolved in ethyl acetate (5.0 L) and stirred at room temperature for 18 hours after which time heptane (0.5 L) was added. The resulting solids were filtered, rinsed with a 2:1 mixture of cold ethyl acetate and heptane (1.5 L total volume), and then dried to yield 976.7 g (80.1%) of (R)-3-(1H-indol-3-yl)-1-[N-(2-methoxybenzyl)amino]-2-(N-triphenylmethylamino)propane.

EXAMPLE 6

Detritylation

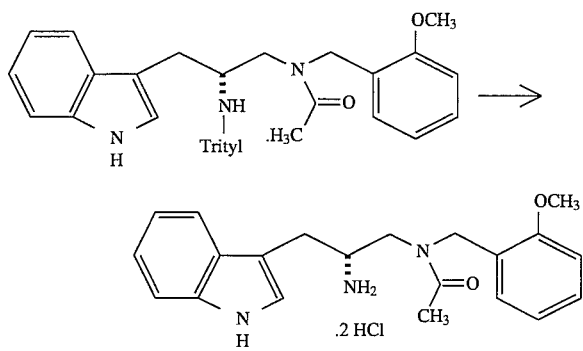

Preparation of (R)-2-amino-3-(1H-indol-3-yl)-1-[N-(2-methoxybenzyl)amino]propane dihydrochloride Under a nitrogen atmosphere (R)-3-(1H-indol-3-yl)-1-[N-(2-methoxybenzyl)amino]-2-(N-triphenylmethylamino)p e (975 g, 1.64 mol) was added to methylene chloride (1.95 L) and cooled to −40° C. to −50° C. Anhydrous hydrogen chloride (0.28 kg, 7.67 mol) was slowly added to this solution and then it was stirred at −10° to 0° C. for 30–60 minutes. Methyl t-butyl ether (1.95 L) was added and the solution was stirred at −10° to 0° C. for an additional 30–60 minutes. The resulting solids were filtered off and rinsed with methyl t-butyl ether (1.5 L), and then dried to yield 659.4 g (94.6 %) of (R)-2-amino-3-(1H-indol-3-yl)-1-[N-(2-methoxybenzyl)amino]propane dihydrochloride.

EXAMPLE 7

Preparation of 2-(4-(piperidin-1-yl)piperidin-1-yl)acetic acid, potassium salt

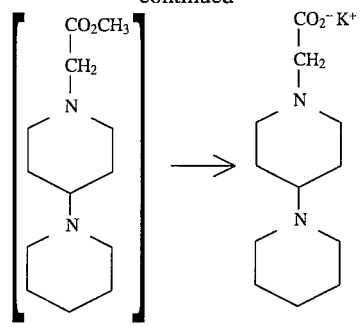

4-(Piperidin-1-yl)piperidine (1.20 kg, 7.13 mol) was added to methylene chloride (12.0 L) under a nitrogen atmosphere. Tetrabutylammonium bromide (0.150 kg, 0.47 mol) and sodium hydroxide (1.7 L of a 5N solution, 8.5 mol) were then added. The reaction mixture was cooled to 10°–15° C. and methyl bromoacetate (1.17 kg, 7.65 mol) was added and the resulting mixture was stirred for a minimum of 16 hours.

Deionized water (1.2 L) was then added to the mixture and the layers separated. The aqueous layer was back-extracted with methylene chloride (2.4 L). The organic fractions were combined and washed with deionized water (3×1.2 L), a saturated sodium bicarbonate solution (1.1 L) and a saturated sodium chloride solution (1.1 L). The organic fraction was then dried over anhydrous magnesium sulfate and concentrated to an oil on a rotary evaporator to yield 1.613 kg (93.5%) of methyl 2-(4-(piperidin-1-yl)piperidin-1-yl)acetate.

A solution of methyl 2-[4-(piperidin-1-yl)piperidin-1-yl] acetate (2.395 kg, 9.96 mol) in methanol (2.4 L) was added to a solution of potassium hydroxide (0.662 kg, 10.0 mol @ 85% purity) in methanol (10.5 L) under a nitrogen atmosphere. The reaction mixture was heated to 45°–50° C. for a minimum of 16 hours.

A solvent exchange from methanol to acetone (15.0 L) was performed on the solution on a rotary evaporator. This solution was slowly cooled to room temperature over 16 hours. The resulting solids were filtered, rinsed with acetone (5.0 L) and then dried to yield 2.471 kg (93.8%) of 2-(4-(piperidin-1-yl)piperidin-1-yl)acetic acid, potassium salt. MS 265 (M$^{+1}$)

EXAMPLE 8

Preparation of (R)-3-(1H-indol-3-yl)-1-[N-(2-methoxybenzyl)acetylamino]-2-[N-(2-(4-(piperidin-1-yl)piperidin-1-yl)acetyl)amino]propane dihydrochloride trihydrate

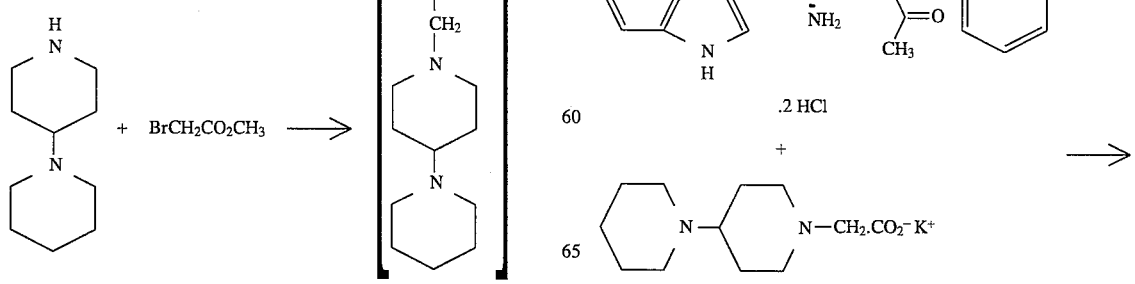

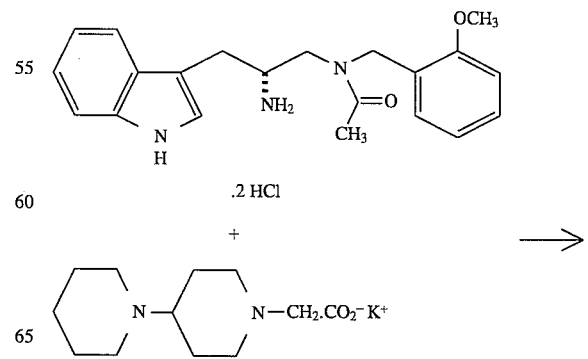

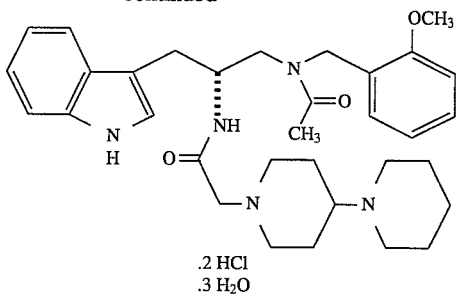

.2 HCl
.3 H₂O

Under a nitrogen atmosphere 2-(4-(piperidin-1-yl)piperidin-1-yl)acetic acid, potassium salt (0.75 kg, 2.84 mol) was added to methylene chloride (7.5 L). The resulting mixture was cooled to −15° to −8° C. and isobutyl chloroform ate (0.29 kg, 2.12 mol) was added at such a rate so as to maintain the temperature of the reaction mixture below −8° C. After the addition the resulting reaction mixture was stirred for 90 minutes between −15 and −8° C.

The reaction mixture was then cooled to −35° C. and solid (R)-2-amino-3-(1H-indol-3-yl)-1-[N-(2-methoxybenzyl)amino]propane dihydrochloride (0.60 kg, 1.14 mol) was added at such a rate that the reaction temperature was maintained at less than −20° C. After the addition, the reaction mixture was stirred for about one hour with the temperature being maintained between −37° C. and −20° C. The reaction was quenched by the addition of deionized water (7.5 L). The reaction mixture was basified to pH 12.8–13.2 by the addition of 5N sodium hydroxide. The aqueous fraction was removed and retained. Additional deionized water (3.75 L) was added to the organic fraction as was sufficient 5N sodium hydroxide to re-adjust the pH to 12.8–13.2.

The two aqueous fractions were combined, back-extracted with methylene chloride (1.5 L) and then discarded. The organic fractions were combined and washed with deionized water (4×3.5 L). These extracts were combined, back-extracted with methylene chloride (1.5 L), and then discarded. The two organic layers were combined and washed with a saturated sodium chloride solution (3.7 L).

The organic fraction was dried over anhydrous magnesium sulfate, filtered, and solvent exchanged from methylene chloride to acetone (3.75 L) on a rotary evaporator. An aqueous solution of hydrochloric acid (0.48 L of 6N solution, 2.88 mol) and seed crystals (2 g) were added and mixture was stirred for 30–90 minutes. Acetone (13.2 L) was then added and the slurry stirred for one hour. The resulting solid was then filtered, washed with acetone (2×1.4 L), and dried to yield 633 g (90%) of (R)-3-(1 H-indol-3-yl)-1-[N-(2-methoxybenzyl)acetylamino]-2-[N-(2-(4-(piperidin-1-yl) acetyl)amino]propane dihydrochloride trihydrate.

The compounds prepared in the present invention are useful as tachykinin receptor-binding compounds. As such, they may be employed as antagonists or agonists of the various tachykinins. These compounds are, therefore, useful in the treatment or prevention of conditions associated with an excess or deficiency of tachykinins. The term "physiological disorder associated with an excess or deficiency of tachykinins" encompasses those disorders associated with an inappropriate stimulation of tachykinin receptors, regardless of the actual amount of tachykinin present in the locale.

These physiological disorders may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative coliris, Crohn's disease and irritable bowel syndrome; disorders of bladder function such as bladder detrusor hyperreflexia and incontinence; atherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Reynaud's disease; emesis; and pain or nociception, for example, that attributable to or associated with any of the foregoing conditions, especially the transmission of pain in migraine. For example the compounds of Formula I may suitably be used in the treatment of disorders of the central nervous system such as anxiety, psychosis, and schizophrenia; neurodegenerative disorders such as Alzheimer's disease and Down's syndrome; respiratory diseases such as bronchospasm and asthma; inflammatory diseases such as inflammatory bowel disease, osteoarthritis and rheumatoid arthritis; adverse immunological disorders such as rejection of transplanted tissues; gastrointestinal disorders and diseases such as disorders associated with the neuronal control of viscera such as ulcerative coliris, Crohn's disease and irritable bowel syndrome; incontinence; disorders of blood flow caused by vasodilation; and pain or nociception, for example, that attributable to or associated with any of the foregoing conditions or the transmission of pain in migraine.

The results of several experiments demonstrate that many of the compounds of Formula I are selective tachykinin receptor antagonists. These compounds preferentially bind one tachykinin receptor subtype compared to other such receptors. Such compounds are especially preferred.

For example, NK-1 antagonists are most especially preferred in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, sunburn pain, neuropathic pain, opioid-resistant pain, visceral pain, surgical pain, bone injury pain, pain during labor and delivery, pain resulting from burns, post parrum pain, angina pain, and genitourinary tract-related pain including cystiris.

In addition to pain, NK-1 antagonists are especially preferred in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; atherosclerosis; inflammatory conditions, such as inflammatory bowel disease, ulcerative coliris, Crohn's disease, rheumatoid arthritis, osteoarthritis, neurogenic inflammation, allergies, rhinitis, cough, dermatitis, urticaria, psoriasis, conjunctivitis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

NK-2 antagonists are especially preferred in the treatment of urinary incontinence, bronchospasm, asthma, adult respiratory distress syndrome, motility disorders of the gastrointestinal tract, such as irritable bowel syndrome, and pain.

In addition to the in vitro binding assays described supra, many of the compounds prepared by the processes of the present invention have also been tested in in vivo model systems for conditions associated with an excess of tachykinins. Of those compounds tested in vivo many have shown efficacy against said conditions.

We claim:

1. The compound (R)-3-(1H-indol-3-yl)-1-[N-(2-methoxybenzyl)acetylamino]-2-[N-(2-(4-(piperidin-1-yl)piperidin-1-yl)acetyl)amino]propane dihydrochloride trihydrate.

2. A pharmaceutical formulation comprising as an active ingredient the compound of claim 1, associated with one or more pharmaceutically acceptable carriers, diluents, or excipients therefor.

3. A method of treating asthma in a mammal comprising administering to said mammal a neurokinin receptor antagonistic effective amount of a compound of claim 1.

* * * * *

UNITED STATES PATENT AND TRADEMARK OFFICE
CERTIFICATE OF CORRECTION

PATENT NO. : 5,530,009

DATED : June 25, 1996

INVENTOR(S) : Cho, et al.

It is certified that error appears in the above-identified patent and that said Letters Patent is hereby corrected as shown below:

On the Title page, item [54] and
Column 1, line 1 "BISPIPERIDINYL NON-PEPTIDYL NEUROKININ RECEPTOR ANTAGONISTS" should read --N,N'-DIACYLPROPANEDIAMINO TACHYKININ RECEPTOR ANTAGONIST--

Column 7, Line 42 "4cyclohexylpiperazine" should read --4-cyclohexylpiperazine--

Column 17, Line 14, "methoxybenzyl" should be deleted.

Column 21, Line 39, "acid white solid" should read --acid as a white solid--

Column 23, Line 38, "p e", should read --propane--

Signed and Sealed this

Twelfth Day of May, 1998

Attest:

BRUCE LEHMAN

Attesting Officer

Commissioner of Patents and Trademarks